United States Patent [19]

Sobel

[11] 3,998,903
[45] Dec. 21, 1976

[54] ALKYLATION WITH SEPARATE BUTENE STREAMS INCLUDING ISOBUTYLENE

[75] Inventor: Jay E. Sobel, Highland Park, Ill.

[73] Assignee: UOP Inc., Des Plaines, Ill.

[22] Filed: Jan. 12, 1976

[21] Appl. No.: 648,235

[52] U.S. Cl. .................... 260/683.48; 260/683.49
[51] Int. Cl.$^2$ ............................................ C07C 3/54
[58] Field of Search ................. 260/683.48, 683.49

[56] References Cited

UNITED STATES PATENTS

| 2,322,800 | 6/1943 | Frey ............................ | 260/683.48 |
| 2,467,731 | 4/1949 | Dart et al. .................... | 260/683.48 |
| 3,560,587 | 2/1971 | Borst, Jr. ..................... | 260/683.48 |
| 3,778,489 | 12/1973 | Parker et al. ................. | 260/683.48 |
| 3,810,955 | 5/1974 | Sobel ........................... | 260/683.49 |

Primary Examiner—George Crasanakis
Attorney, Agent, or Firm—James R. Hoatson, Jr.; Thomas K. McBride; William H. Page, II

[57] ABSTRACT

A process for producing an alkylation reaction product from an isoparaffin and an olefinic reactant containing 1-butene, 2-butene and isobutylene by fractionating the olefinic reactant into a 2-butene fraction and a separate 1-butene and isobutylene fraction. The 2-butene is charged to an HF alkylation reaction zone with isobutane. The mixture is heated by the endothermic reaction, and the fraction comprising 1-butene and isobutylene is then added to the unitary reaction zone. It is possible to alkylate these olefins at conditions which are close to the optimum conditions, using a single reactor vessel, which operates at different temperatures without the necessity for heat exchange means.

7 Claims, 1 Drawing Figure

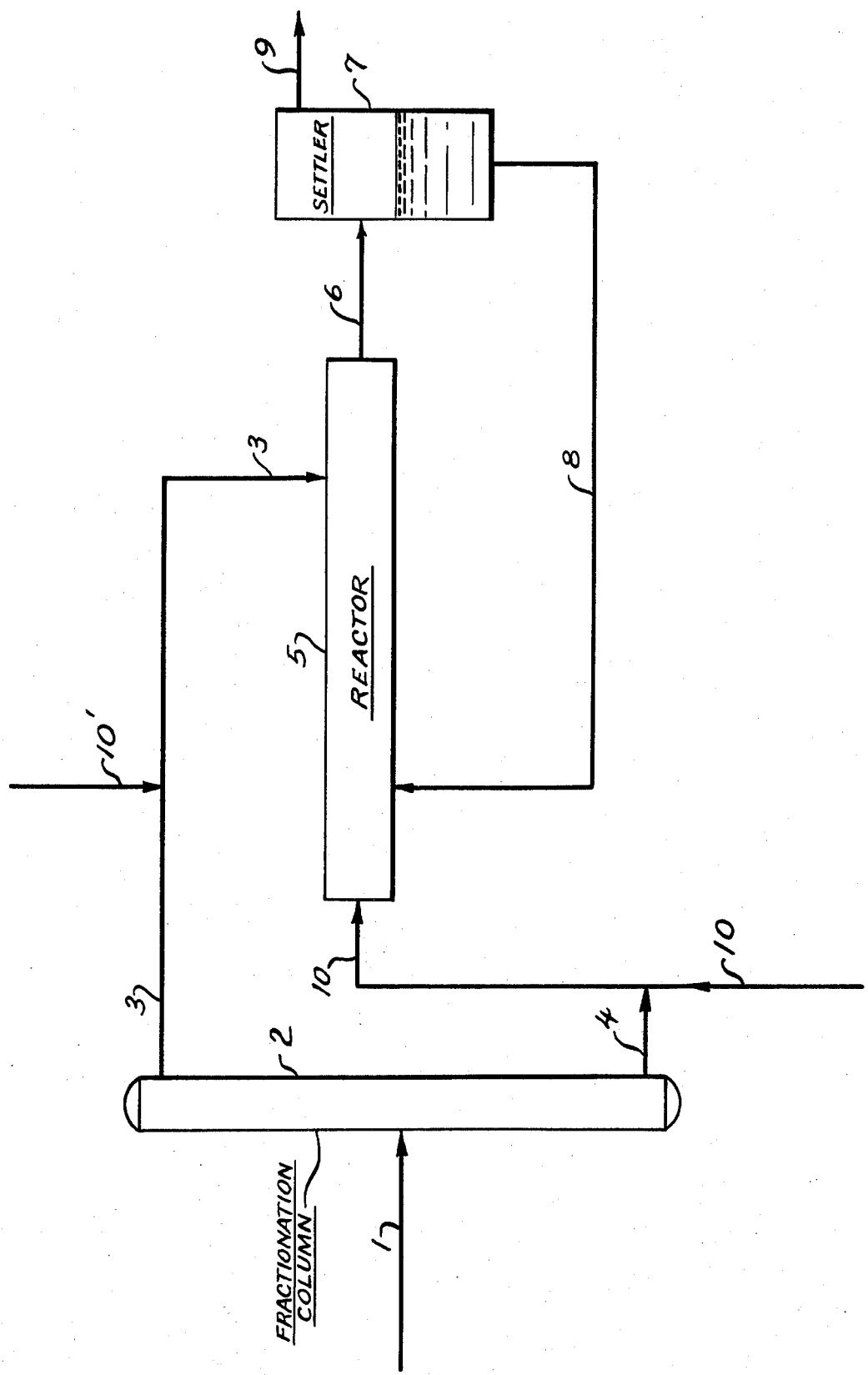

ALKYLATION WITH SEPARATE BUTENE STREAMS INCLUDING ISOBUTYLENE

BACKGROUND OF THE INVENTION

1. Field of the Invention

The invention relates to an improved HF alkylation process wherein an isoparaffin reactant, preferably isobutane, is reacted with $C_4$ monoolefins in the presence of liquid phase HF alkylation catalyst.

2. Prior Art

The use of catalytic alkylation to produce gasoline boiling range isoparaffins is well known in petroleum refining. Generally, the alkylation of isoparaffins with olefins is accomplished by contacting the reactants with an acid acting catalyst such as hydrogen fluoride or sulfuric acid, settling the mixture to separate the catalyst from hydrocarbons, and further separating the hydrocarbons, e.g., by fractionation to recover alkylate product. Alkylate is typically a mixture of isomers of heptane, octane, etc., with the exact composition depending upon the isoparaffin and olefin reactants used. In commercial alkylation processes, the isoparaffin is normally isobutane, while the olefin reactant is usually a mixture of $C_4$ olefins, e.g., 1-butene, 2-butene and isobutylene, or a mixture of these olefins with amylenes and/or propylene.

I recognized in my U.S. Pat. No. 3,810,955 (Class 260-683.49), the teachings of which are incorporated by reference, that there is an antagonism between 1-butene and isobutylene in the HF alkylation process. I solved this problem by separating, via an adsorptive separation process, the undesirable 1-butene fraction from the $C_4$ mono-olefins. Although the beneficial effect of removing 1-butene from the feed was a very significant one, the cost of the adsorptive separation zone was such that in some instances, e.g., very small units, it was not economically justifiable to perform this process, which called for the use of two separate alkylation zones.

I have now found a way to minimize the antagonism between 1-butene and isobutylene in an alkylation process while performing the alkylation in a single reaction zone.

Accordingly, the present invention provides a process for alkylating an isoparaffin with a stream comprising 2-butene and a separate stream comprising 1-butene and isobutylene which comprises (a) passing at least a portion of the isoparaffin in admixture with the 2-butene stream and HF acid catalyst to an upstream portion of a reactor wherein the 2-butene reacts with the isoparaffin in an exothermic reaction which increases the temperature of the reactants, acid, and alkylate, (b) charging to a downstream portion of the reactor a stream comprising 1-butene and isobutylene, (c) withdrawing from the reactor alkylate products, unreacted isoparaffins, and HF catalyst.

The feedstocks, and other details of the alkylation process are well known in the art, and are given in detail in my above-mentioned U.S. Pat. No. 3,810,995. The conditions must, of course, be modified somewhat, because in the practice of the present invention the 1-butene is alkylated with isobutylene. The reaction conditions are chosen so that the alkylation of each olefin fraction will occur in a single reactor vessel at close to optimum conditions for each fraction of olefin. The optimum temperature for alkylation of 2-butene is lower than the optimum temperature for the alkylation of a mixture of isobutylene and 1-butene. The 2-butene is added first to the reaction zone, which is preferably an elongated reaction zone. The alkylation reaction is exothermic. In the reactor, which preferably operates adiabatically, i.e., without a heat exchanger means, the exothermic reaction heats up the material in the reactor. The higher temperature provides close to optimum conditions for the alkylation of isobutylene and 1-butene in a downstream portion of the reactor.

The acid strength and type can be basically that discussed in my U.S. Pat. No. 3,810,955, previously discussed. The optimum reaction conditions for the 2-butene alkylation include a temperature of 0° to 25° C, pressure sufficient to maintain liquid phase, and a contact time between catalyst and hydrocarbon of 0.1 to 5 minutes. The isoparaffin to olefin ratio may be from 2:1 to 20:1, with the volume ratio of catalyst to hydrocarbons being from 0.1:1 to 10:1.

The optimum conditions for alkylating the mixture of isobutylene and 1-butene include a temperature of 25° to 50° C, pressure sufficient to maintain liquid phase, a catalyst:hydrocarbon contact time of about 5 to 30 minutes, and an isoparaffin to olefin ratio of 2:1 to 20:1. Additional isoparaffin reactant may be added to the reactor, or added to the stream containing isobutylene and 1-butene, to make up for the amount of isoparaffin consumed in the alkylation of 2-butene. Slightly higher ratios of isoparaffin to olefin are believed optimum for the alkylation of isobutylene plus 1-butene, than for the alkylation of 2-butene. However, because of the unique reactor configuration of the present invention, in one embodiment, all the isoparaffin reactant is added to the reactor inlet. The relatively high isoparaffin to olefin occurring there improves the quality of the 2-butene alkylate, and there is no great incremental expense in circulating all of the isoparaffin through the entire length of the reactor. It should be noted that the total isoparaffin to total olefin ratio can be significantly less in the practice of the present invention than in a prior art process, not only because the olefins are separated and alkylated at optimum conditions for each olefin species, but also because the 2-butene olefin is completely reacted by the time the isobutylene and 1-butene olefin species is added. Thus, the isoparaffin to olefin ratio that the olefins in the reactor experience can be much higher than in prior art reaction designs where the entire amount of olefin is added at the inlet to a reactor. However, simple multipoint injection of the olefin feed stream into the reactor is not my invention.

The amount of temperature increase which will be experienced is a function not only of the amount of olefin and isoparaffin which reacts, but also of the amount of other material around which acts as a heat sink. Increasing the isoparaffin to olefin ratio will decrease the temperature increase experienced as reactants pass through the reactor. Similarly, increasing the acid to hydrocarbon ratio will decrease the amount of temperature increase. Those skilled in the art know that changing the isoparaffin to olefin ratio also changes the quality and character of the motor fuel alkylate produced. Thus, changing the isoparaffin to olefin ratio would shift the product distribution even if the reaction zone was maintained under isothermal conditions. In the present invention, shifting this ratio causes the same change, and in addition changes the temperature of the downstream reaction zone, which also has an effect on alkylate.

Further, shifting the point of isoparaffin addition, from all to only a fraction of the isoparaffin being added at the inlet to the reactor, also changes the residence time within the reactor.

Intergrating the discussion of these variables, the optimum reactor conditions are believed to be:
Acid/hydrocarbon: 3/2
Isobutane/olefin: 12/1
Inlet 2-$C_4^=$ temp.: 20° C.
Acid 89%; HF 10%; OD 1% $H_2O$.

BRIEF DESCRIPTION OF THE DRAWING

The attached drawing is a schematic representation of one embodiment of the present invention wherein a mixture of $C_4$ olefins is separated in a fractionation column, and then fed separately to an elongated alkylation reactor.

DETAILED DESCRIPTION

A mixed olefin feed stream, comprising a mixture of 1-butene, 2-butene and isobutylene is fed via line 1 into fractionation column 2. The isobutylene and 1-butene are recovered as an overhead fraction via line 3, while the 2-butene is recovered as a bottoms fraction via line 4. Isobutane is added via line 10 to the 2-butene stream contained in line 4, and the mixture charged to the inlet of elongated alkylation reaction zone 5. A liquid catalyst phase comprising HF acid, small amounts of water, and organic diluent, is added to the reactor via line 8. Alkylation reactor 5 is of conventional design, and includes baffles and other distributing means within the reactor to insure good contact of olefins, isoparaffin, and catalyst. The olefins recovered as an overhead fraction via line 3 are added to a downstream portion of reactor 5 via line 3. Additional isobutane is added to line 3 via line 10'. The reactor effluent is removed via line 6 and charged to settler 7, wherein an acid phase is recovered and recycled via line 8 to the reactor. The hydrocarbon phase is removed via line 9 and sent to conventional alkylate recovery systems.

Not shown in the drawing are pumps, valves, or any details of the fractionators, or settlers, as these devices are all well known in the art. Also not shown are any feed pretreatment facilities, such as driers or fractionators used to obtain an olefin stream comprising $C_4$ mono-olefins. Also not shown are conventional downstream facilities, such as alkylate soakers, wherein either entrained or added HF acid promotes conversion of alkyl fluorides into more desirable compounds, or conventional product fractionation facilities. In most commercial embodiments, the excess isobutane not consumed in the reaction zone will be recovered in a fractionator and recycled by means not shown to lines 10 and 10'.

In other embodiments, a solid bed alkylation catalyst, e.g., $AlCl_3$, $BF_3$, SPA, or other suitable catalyst which will alkylate isoparaffins with $C_4$ mono-olefins may be used. Similarly, sulfuric acid catalyst may be used, though the optimum operating conditions existing in the reactor will probably have to be adjusted somewhat.

ILLUSTRATIVE EMBODIMENT

The effect of reaction temperature was studied using as feed 1-butene, 2-butene, and mixtures of isobutylene and 1-butene. First the effects of changing reactor temperature on the alkylation of 1-butene or 2-butene was studied. The test conditions included an acid to hydrocarbon volume ratio of 3/2, an isobutane to olefin mole ratio of 12 to 1, and use of HF acid containing 10 wt. % organic diluent and 1 wt. % $H_2O$. The base temperature was 20 C, and temperature variations ranging up to plus or minus 5° C were tested. As applied to the alkylation of 1-butene, increasing the temperature by 5° C increased the research octane number by 0.19, the motor octane number by 0.35 and the TMP/DMH (trimethylpentane/dimethylhexane) ratio by 0.18. Alkylation of 1-butene at these conditions at 20° C produces alkylate with a research octane number of 93.16, a motor octane number of 91.7, and a TMP/DMH ratio of 2.89. Operation at 25° C will produce an alkylate with a research octane number of 93.35, a motor octane number of 92.05 and a TMP/DMH ratio of 3.07.

A similar study was made using 2-butene as a feed. The base conditions produced an alkylate with a research octane number of 99.01, a motor octane number of 95.81, and a TMP/DMH ratio of 14.31. Increasing the temperature 5° C resulted in a decrease of 0.64 from the research octane, a decrease of 0.41 from the motor octane number, and a decrease of 4.63 from the TMP/DMH ratio. Thus, operating the reactor at 15° C would produce an alkylate with a research octane number of 99.65, a motor octane number of 96.22 and a TMP/DMH ratio of 18.94.

Tests were next conducted using a 50/50 volumetric mixture of isobutylene and 1-butene. These experiments indicated that increasing the temperature at which the alkylation reaction occurred did increase the octane number. Unfortunately, the water content, and organic diluent content of the reaction zone acid phase were also changed, so the test is not conclusive.

Based upon these studies, it is believed that in a commercial HF alkylation unit wherein the present invention is practiced using an acid to hydrocarbon volume ratio of 1.25:1 and an isobutane to olefin mole ratio of 12:1 considering total olefin feed to the reactor or a ratio of 24:1 considering only the olefin in the upstream portion of the reactor, the operating conditions should be as follows. A slightly lower acid to hydrocarbon ratio is used, to decrease the amount of isomerization of 2-butene which occurs in the reaction zone, and also to augment the temperature rise to be experienced going through the reactor. Based on an olefin feed consisting of 22 mole % 1-butene, 50 mole % 2-butene, and 28 mole % isobutylene, the temperature is preferably 20° C, or colder if ample chilled water is available for cooling feed and acid entering the reactor. The reactor operates adiabatically, and the temperature increase due to the reaction of 2-butene is about 10° C. The isobutylene and 1-butene stream is charged to the reactor in the final 40% thereof via multiple feed-point injection. The reactor effluent is passed to a conventional settler and other downstream processing units. The product alkylate octane number is expected to be about 94.0. In contrast, if the olefins were merely added, via multiple feed-point injection, to a conventional reactor operating isothermally at 25° C, the product alkylate octane number would be 95.0. Further a conventional reactor would cost more to build, because a heat exchanger is required for adiabatic operation.

I claim as my invention:
1. A process for alkylating an isoparaffin with a stream comprising 2-butene and a separate stream comprising 1-butene and isobutylene which comprises a. passing at least a portion of the isoparaffin in admixture with the 2-butene stream and HF acid catalyst to an upstream portion of a reactor wherein the 2-butene reacts with the isoparaffin in an exothermic reaction which increases the temperature of the reactants, acid, and alkylate,
b. charging to a downstream portion of the reactor a stream comprising 7-butene and isobutylene,
c. separating a hydrocarbon phase comprising alkylate products and unreacted isoparaffins; from HF catalyst phase, and
d. separating said alkylate products from said hydrocarbon phase of step (c).

2. Process of claim 1 wherein the reactor is a single, elongated vessel.

3. Process of claim 1 wherein the reactor operates adiabatically.

4. Process of claim 1 wherein the isoparaffin reactant is isobutane, and the isobutane is supplied in a molar ratio equivalent to 2:1 to 24:1, based upon the total amount of olefin charged to the reactor.

5. Process of claim 1 wherein the acid to hydrocarbon ratio in the reactor is 1:1 to 2:1.

6. Process of claim 1 wherein the temperature difference between said upstream portion and said downstream portion of the reactor is 1° to 10° C.

7. Process of claim 1 wherein additional isoparaffin is charged to said downstream portion of the reactor.

* * * * *